United States Patent
Van Apeldoorn et al.

(10) Patent No.: US 9,422,524 B2
(45) Date of Patent: Aug. 23, 2016

(54) DIABETES TREATMENT

(75) Inventors: Aart Alexander Van Apeldoorn, Utrecht (NL); Hermanus Bernardus Johannes Karperien, Eibergen (NL); Clemens Antoni Van Blitterswijk, Ruigahuizen (NL); Eelco Johan Paul De Koning, Bussum (NL); Marten Alexander Engelse, Oegstgeest (NL)

(73) Assignees: UNIVERSITEIT TWENTE, Enschede (NL); ACADEMISCH ZIEKENHUIS LEIDEN H.O.D.N. LUMC, Leiden (NL)

( * ) Notice: Subject to any disclaimer, the term of this patent is extended or adjusted under 35 U.S.C. 154(b) by 879 days.

(21) Appl. No.: 13/391,269

(22) PCT Filed: Aug. 17, 2010

(86) PCT No.: PCT/NL2010/050517
§ 371 (c)(1),
(2), (4) Date: May 30, 2012

(87) PCT Pub. No.: WO2011/021933
PCT Pub. Date: Feb. 24, 2011

(65) Prior Publication Data
US 2012/0251587 A1  Oct. 4, 2012

(30) Foreign Application Priority Data
Aug. 17, 2009 (EP) .................................. 09168007

(51) Int. Cl.
| A61K 9/00 | (2006.01) |
| C12N 5/071 | (2010.01) |
| A61K 35/39 | (2015.01) |
| A61L 27/18 | (2006.01) |
| A61L 27/38 | (2006.01) |
| A61L 27/56 | (2006.01) |
| C12N 5/00 | (2006.01) |

(52) U.S. Cl.
CPC ............. *C12N 5/0677* (2013.01); *A61K 35/39* (2013.01); *A61L 27/18* (2013.01); *A61L 27/3804* (2013.01); *A61L 27/3839* (2013.01); *A61L 27/56* (2013.01); *C12N 5/0068* (2013.01); *C12N 2533/30* (2013.01)

(58) Field of Classification Search
CPC ............... A61L 27/18; A61L 27/3804; A61L 27/3839; A61L 27/56; C12N 2533/30; C12N 5/0068; C12N 5/0677; C08L 71/02; A61K 35/39
See application file for complete search history.

(56) References Cited

U.S. PATENT DOCUMENTS

| 8,435,781 B2* | 5/2013 | Kodama ................ 435/299.1 |
| 2003/0096408 A1 | 5/2003 | Gerber et al. |
| 2003/0175410 A1* | 9/2003 | Campbell et al. ........... 427/2.24 |
| 2008/0103606 A1* | 5/2008 | Berkland et al. .......... 623/23.72 |
| 2010/0233239 A1 | 9/2010 | Berkland et al. |

FOREIGN PATENT DOCUMENTS

| JP | 2008-278769 | 11/2008 |
| WO | WO-03/057271 | 7/2003 |

OTHER PUBLICATIONS

Blomeier ("Polymer Scaffolds as Synthetic Microenvironments for Extrahepatic Islet Transplantation," Transplantation. Aug. 27, 2006; 82(4): 452-459).*
International Search Report for PCT/NL2010/050517, mailed Sep. 30, 2010, 3 pages.

* cited by examiner

*Primary Examiner* — Suzanne Ziska
(74) *Attorney, Agent, or Firm* — Morrison & Foerster LLP

(57) ABSTRACT

The invention is directed to a treatment of diabetes, a scaffold and a method of preparing a scaffold. In a first aspect, this object is met by providing a scaffold comprising beta cell aggregates, wherein the aggregates are distributed over the scaffold in a predetermined pattern.

20 Claims, 6 Drawing Sheets

Fig. 5 A-D

DIABETES TREATMENT

CROSS-REFERENCE TO RELATED APPLICATIONS

This application is the national phase of PCT application PCT/NL2010/050517 having an international filing date of 17 Aug. 2010, which claims benefit of European patent application No. 09168007.4 filed 17 Aug. 2009. The contents of the above patent applications are incorporated by reference herein in their entirety.

The invention is directed to a treatment of diabetes, a scaffold and a method of preparing a scaffold.

Diabetes mellitus (diabetes) is a condition in which the body does not produce enough, or does not properly respond to, insulin. Insulin is a hormone produced in the pancreas which enables cells to absorb glucose in order to turn it into energy. In diabetes, the body may not respond properly to its own insulin and/or does not make sufficient amounts of insulin. This causes glucose to accumulate in the blood, often leading to various complications.

Diabetes occurs in different forms. The main three types of diabetes are type 1 (see hereinbelow), type 2 and gestational diabetes. Type 2 diabetes results from insulin resistance, a condition in which cells fail to use insulin properly, sometimes combined with relative insulin deficiency. Gestational diabetes is found in pregnant women who have never had diabetes before but who have high blood sugar (glucose) levels during pregnancy. Many other forms of diabetes mellitus are categorized separately from these. Examples include congenital diabetes due to genetic defects of insulin secretion, cystic fibrosis-related diabetes, steroid diabetes induced by high doses of glucocorticoids, and several forms of monogenic diabetes.

Diabetes type 1 is an autoimmune disease, in which patients suffer from self-destruction of beta cells. A beta cell is a type of cell in the pancreas in areas called the islets of Langerhans. Beta cells make up 65-80% of the cells in the islets. Beta cells produce and release insulin, a hormone that controls the level of glucose in the blood. Beta cells further produce amylin and also release glucagon and C-peptide, a byproduct of insulin production. As a result of the self-destruction of beta cells, diabetes type 1 patients suffer from hyperglycemia, which is a condition in which an excessive amount of glucose circulates in the blood plasma. Hyperglycemia can ultimately lead to symptoms such as retinopathy, heart and kidney failure, as well as atherosclerosis.

Diabetes type 1 is typically treated with insulin replacement therapy, usually by insulin injection or insulin pump. Currently, there are several therapies available to manage blood glucose levels as a treatment for diabetes type I, like regular insulin injections or automated insulin pumps. Such therapies are experienced unpleasant and interfere with everyday life.

An alternative treatment of diabetes type 1 is the infusion of allogeneic islets of Langerhans isolated from cadaveric donor pancreata into the portal vein. This method is known as the Edmonton Protocol. Disadvantage of this method is that it is rather inefficient in that approximately 80% of the transplanted islets die within a few days after infusion. Furthermore, insulin independence is usually not sustainable in the long term, with typically less than half of the treated patients being insulin independent one year after the treatment. Another disadvantage of the Edmonton Protocol is that multiple, preferably three, donor pancreata are needed for the treatment of one patient. This contributes to the already existing lack organ donors.

US 2003/0096408 describes a cell support system comprising a solid substrate with a plurality of recessed cavities, in which cavities a plurality of live cells is deposited and wherein the live cells consist essentially of nonembryonic hepatic or pancreatic progenitor cells. It is an object of the present invention to solve at least in part the problems encountered in the prior art regarding the treatment of diabetes.

In a first aspect, this object is met by providing a scaffold comprising beta cell aggregates, wherein the aggregates are distributed over the scaffold in a predetermined pattern.

The inventors surprisingly found that using scaffolds of the invention as implants in the body for diabetes treatment may improve the beta cells' survival in the body, in particular when compared to the survival of beta cells in the method according to the Edmonton Protocol.

Figure 1:
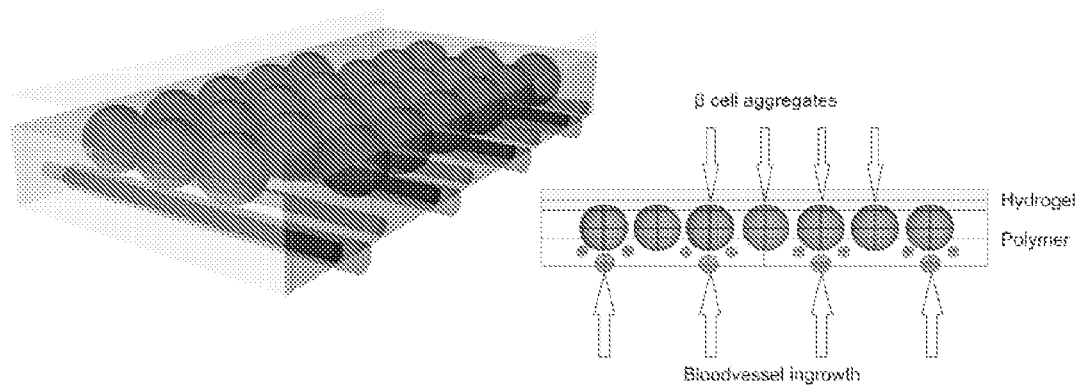
FIG. 1 is a schematic drawing of a scaffold according to the invention.

A scaffold as used herein may refer to an artificial structure capable of supporting three-dimensional tissue formation. An example of a scaffold is an implantable scaffold, e.g. an artificial organ such as an artificial pancreas.

A "beta cell aggregate" as used herein is defined as a conglomeration of two or more cells, of which at least one is a beta cell. A beta cell typically originates from isolated islets of Langerhans. An example of a beta cell aggregate is an islet of Langerhans. An islet of Langerhans may for example be isolated from cadaveric donor pancreata.

A beta cell is a differentiated cell that can be found in an islet of Langerhans. Beta cells are the main insulin controlling regulator in the human body. Preferably, essentially all cells in the beta cell aggregate of the invention are differentiated cells. This is for example the case in an islet of Langerhans.

Islets of Langerhans are irregularly shaped patches of endocrine (hormone-producing) tissue located within the pancreas of most vertebrates. They are named for the German physician Paul Langerhans, who first described them in 1869. The normal human pancreas contains about 1,000,000 islets of Langerhans. The islets consist of at least four distinct cell types, of which three (alpha, beta, and delta cells) produce important hormones; the fourth component (C cells) has no known function. The cells in the islets of Langerhans play a role in insulin regulation.

The advantage of using aggregates comprising differentiated (beta) cells is that they do not, or at least not substantially, exhibit cell growth when present in a scaffold of the invention, for at least as long as the scaffold has not yet been implanted in a living organism. In case undifferentiated cells would be used, such as progenitor cells, the cells would proliferate due to cell division. This has the disadvantage that the size of the aggregates may become too large to be properly held by the microcells, which may result into undesirable merging of beta cell agglomerates of different wells. This may lead in time to uncontrolled differentiation into non-relevant cell types. Furthermore, the aggregate, upon cell growth, may loose the favorable morphology it initially has when placed in the wells of the scaffold. This may lead to dedifferentiation of functional cell types and therefore loss of function.

The beta cell aggregates may be distributed in such a pattern that they are homogeneously distributed over the scaffold. The predetermined pattern may further be a pattern, wherein the distance between any two adjacent beta cell aggregates is the same, which pattern may be homogenously distributed. In another embodiment the aggregates are patterned in parallel rows.

The scaffold comprises beta cell aggregates. The beta cells typically originate from islets of Langerhans. Islets of Langerhans can be isolated from cadaveric donor pancreata. The beta cell aggregates may be provided to the scaffold in the form of islets of Langerhans, which islets are not treated after isolation from the pancreas. Thus, the beta cell aggregate may comprise one or more isolated islets of Langerhans.

The beta cell aggregates according to the invention have a three-dimensional structure. Generally, the beta cell aggregates have an ellipsoidal or globular shape. The size of a beta cell aggregate may be defined by its diameter (in case of a globular shape) or by its large diameter (in case of an ellipsoidal). Such diameters may be determined by using a Scanning Electron Microscope (SEM) or a light microscope. The (large) diameter of the particle may also be determined by filtering the particles with a cell strainer using different mesh sizes.

The beta cell aggregates may comprise artificial beta cell aggregates. An artifical beta cell aggregate is an artificially generated complex of in vitro treated cells derived from islets of Langerhans, which may comprise cells from other sources. The advantage of using artificial beta cell aggregates is that such aggregates can be customized, e.g. by giving the aggregates a certain size. In one embodiment, all beta cell aggregates in the scaffold are artificial.

It was found that beta cell aggregates with a small size may have a better chance of survival after implantation and may produce more insulin than large beta cell aggregates. Therefore, the beta cell aggregates preferably have a diameter less than 350 μm, more preferably a diameter of 250 μm or less, even more preferably a diameter of 150 μm or less, most preferably a diameter of 100 μm or less. Typically, the aggregate has a minimum diameter of at least 20 μm, more preferably at least 50 μm. The diameter of the beta cell aggregates may be determined by using a Scanning Electron Microscope (SEM).

The scaffold is preferably biodegradable, so that it may be absorbed after implantation by the surrounding tissues without the necessity of surgical removal. The materials from which the scaffold is made are each preferably non-cytotoxic. Also, any degradation products of such materials, e.g. as a result of biodegradation, are preferably non-cytotoxic. Furthermore, the scaffold is preferably biocompatible, such that the scaffold may elicit little or no immune response in a given organism when implanted and is able to integrate with the organism's tissue.

Once the scaffold according to the invention has been implanted, the scaffold should allow for sufficient nutrient and insulin transport. This means that the scaffold has to be sufficiently penetrable for blood-vessel ingrowth both for the islets to survive and for the beta cells to be capable of adequately performing their function.

Preferably, the scaffold comprises one or multiple scaffold sheets that are either stacked or non-stacked. A sheet-shape has the advantage that it allows for flexibility, which is important for suitable implantation in a patient. The scaffold may be composed of multiple smaller scaffold sheets, e.g. by stacking sheets or by rolling up sheets. This is practical in surgery, because a scaffold suitable as an implant to treat a patient of, for instance, about 100 kg typically requires dimensions of 10×10 $cm^2$, which may be too large for a single scaffold sheet to cover. In one embodiment, the scaffold itself is also in the form of a sheet, which form is suitable for implantation. Preferably, the scaffold comprises less than 50 scaffold sheets, more preferably less than 40 scaffold sheets, even more preferably less than 30 scaffold sheets, even more preferably less than 20 scaffold sheets, most preferably less than 10 scaffold sheets.

The scaffold sheet preferably has a surface area of 100 $cm^2$ or less, more preferably 50 $cm^2$ or less, even more preferably 25 $cm^2$ or less, most preferably 10 $cm^2$ or less. The surface area may be as small as 0.5 $cm^2$ or even smaller. The surface area of the scaffold sheet may have any suitable shape, but preferably has a square or rectangular shape. For example, the surface area of the scaffold sheet may be 2×2 cm.

The scaffold sheet may comprise a first layer that allows for the formation of beta cell aggregates and the distribution of the beta cell aggregates in a predetermined pattern.

The first layer may comprises a surface comprising microwells. Microwells are small cavities on the surface of the first layer. A microwell structure may promote the formation of beta cell aggregates, because they can hold a certain amount of beta cells and optionally other components.

Preferably, the diameter of each microwell is 20-800 μm, more preferably 40-500 μm, most preferably 100-350 μm. A microwell may have any shape, but is preferably essentially circular shaped. The distance between each microwell is preferably less than 500 μm, more preferably less than 350 μm, even more preferably less than 200 μm, most preferably less than 50 μm. The diameter of a microwell is measured at its open end (or, in case a second layer is present, at the side where the second layer covers the microwell). In case the shape of the microwell at the open end is non-circular, the circumscribed circle may be used as the diameter instead.

The depth of the microwell may be 0.5-2 times the size of its diameter, preferably 8.8-1.2 times the size of its diameter, for example about the same length as its diameter. In one embodiment, the depth of the microwell is 150-200 μm.

An islet of Langerhans typically has a diameter of 100-200 μm. Although islets of Langerhans having a diameter smaller than 100 μm and islets of Langerhans having a diameter bigger than 200 μm may also be found in the pancreas, such islets are in the minority. In case an isolated islet of Langerhans is used, the microwells should be large enough for the islet to fit in. Therefore, in case islets of Langerhans are used as the beta cell aggregate, in particular when such islets are derived directly from a donor pancreas, the microwells preferably have a diameter of at least 50 μm, more preferably at least 100 μm. There is no upper limit for the size of the microwells. However, the larger the size of the microwells, the smaller amount of wells will fit per surface area of the polymer layer. Therefore, the microwells usually have a diameter of 350 μm or smaller.

Preferably, a microwell comprises one islet of Langerhans. However, in case the islets are small (e.g. less than 100 μm), a microwell may also comprise two or even more islets.

Based on the size of the microwells, number of cells in the microwells and the size of the scaffold, a person skilled in the art may deduce and optimize the number of microwells needed on a scaffold suitable as an implant for patients suffering from diabetes.

The size of the agglomerates may be determined by placing a fixed number of beta cells in the wells. To obtain a suitable sized agglomerate, each well may comprise 20-500, preferably 40-400, more preferably 50-200 cells. In case the agglomerate is an islet of Langerhans, each agglomerate may typically comprises a minimum average of at least 50 cells (for example at least 200 or at least 400 cells) and a maximum average of 4000 cells or less (for example 2500 cells or less or 1500 cells or less). Preferably, at least 20% of these cells are beta cells, more preferably at least 50%, even more preferably at least 70%, most preferably at least 90%. The scaffold preferably comprises at least 1 million microwells and at most 5 million microwells. From these data, one could calculate the total number of beta cells present in a scaffold according to the invention. The scaffold sheet may further comprise a second layer for protection of the beta cells after implantation. The second layer may contain and protect the non adhered beta cell aggregates during handling by tissue culture, implantation and/or after implantation. The second layer may form an immunoevasive layer, which prevents so-called T-cells from invading and degrading the beta cells after implantation of the scaffold in the body, which in turn might cause immune rejection and thus failure of the implant. A hydrogel layer was found to be very suitable as a second layer.

FIG. 1 is a schematic representation of a scaffold according to the invention. The first layer consist of a porous polymer sheet (grey-white) in which microwells are present) of such a size that isolated islets of Langerhans can fit into these wells (depicted as large dark grey colored spheres). The wells are covered with a hydrogel layer (depicted in light grey). Due to the porosity of the first layers, bloodvessels are allowed to penetrate the scaffold and support the Islets of Langerhans with vasculature for nutrient supply (depicted by small gray circles).

In case the first layer comprises microwells, the second layer has the further function of keeping the agglomerates in the microwells in place, e.g. by covering the microwells with the second layer. The second layer may thus form a semipermeable layer, which prevents the release of aggregates from the microwells but is fully permissible for nutrient and waste product exchange as well as cell ingrowth.

Preferably, the adhesion between the beta cell aggregates and the microwell inner surface is low to such an extent, that the morphology of the beta cell aggregates is not substantially influenced by adhesive forces with the wall. For this purpose, the microwell inner surface is preferably constructed from a material that has anti-adhesive properties with respect to the beta cell aggregates. The low adhesion between the aggregates and the microwell inner surface thus helps the aggregate maintain its favorable initial morphology, in particular when the beta cell aggregate is an islet of Langerhans. Furthermore, in case a seeding method is used wherein beta cell aggregates are formed from individual cells in the microwells, such as in the centrifugation and hanging drop methods described below, the low adhesion can promote the formation of beta cell aggregates.

For the purpose of decreasing adhesion, the inner surface of the microwells may be chemically treated prior to adding the beta cell aggregates.

In a preferred embodiment, the material used for the microwell inner surface and the material from which the first layer is constructed is the same.

For example, the first layer may be a hydrophobic layer. Typically, cell material, such as beta cells and islets of Langerhans, are hydrophilic. In a hydrophobic first layer, cells can only adhere to each other and not to the first layer, e.g. cells residing in microwells made of hydrophobic material can only adhere to each other and not to the hydrophobic surface of the microwells.

Furthermore, the first layer is preferably viscoelastic in order for the scaffold to be suitable used as an implant.

Typically, the first layer is a polymer layer. Based on the preferences (hydrophobicity, viscoelasticity, biodegradability, biocompatibility, etc.) of the polymer for the first layer described hereinabove, only a small number of polymers are suitable. Examples of suitable polymers are polylactic acid (PLA), polypropylene (PP), polycarbonate (PC), cyclic olefin polymer (COP), poly(trimethylene carbonate), caprolactone, poly(lactic-co-glycolic acid) (PLGA), polyurethane (PU), PU derived biomaterials and copolymer of a polyalkylene glycol terephtalate and an aromatic polyester.

Preferably, the first layer is made of a copolymer of a polyalkylene glycol terephtalate and an aromatic polyester, such as desribed in EP-A-1 247 537. It is one of the great advantages of this copolymer that the composition of the copolymer may be adjusted such as to achieve a good adhesion to nearly any type of material. The nature and molecular weights of the monomers of the copolymer, as well as the ratio of the two monomers and the molecular weight of the copolymer itself, provide a multitude of variations that can be used to achieve an optimum property profile of the first polymer layer. These parameters do not only serve to adjust the adhesion of the coating. Other properties can be optimised as well. Examples of such properties include the degradability and swelling behaviour of the polymer and mechanical properties, like elasticity and tensile strength. Other properties and advantages will become clear from the following, more detailed description of the copolymer.

Preferably, the copolymer comprises 20-90 wt. %, more preferably 40-70 wt. % of the polyalkylene glycol terephtalate, and 80-10 wt. %, more preferably 60-30 wt. % of the aromatic polyester. A preferred type of copolymers according to the invention is formed by the group of block copolymers.

The polyalkylene glycol may have a weight average molecular weight of about 150 to about 10000. Preferably, the polyalkylene glycol has a weight average molecular weight of 200 to 4000. The aromatic polyester preferably has a weight average molecular weight of from 200 to 9000, more preferably from 250 to 4000. The weight average molecular weight of the copolymer preferably lies between 10,000 and 300,000, more preferably between 40,000 and 120,000.

The weight average molecular weight may suitably be determined by gel permeation chromatography (GPC). This technique, which is known per se, may for instance be performed using chloroform, hexafluoro isopropanol or m-cresol as a solvent and polystyrene as external standard. Alternatively, a measure for the weight average molecular weight may be obtained by using viscometry (see NEN-EN-ISO 1628-1). This technique may for instance be performed at 25° C. using chloroform as a solvent. Preferably, the intrinsic viscosity of the copolymer lies between 0.2 and 1.5 dL/g, which corresponds to a weight average molecular weight between 10,000 and 300,000. Likewise, the more preferred ranges for the weight average molecular weight measured by GPC mentioned above can also be expressed in terms of the intrinsic viscosity.

In a preferred embodiment, the polyalkylene glycol terephtalate component has units of the formula —OLO—CO-Q-CO—, wherein O represents oxygen, C represents carbon, L is a divalent organic radical remaining after removal of terminal hydroxyl groups from a poly(oxyalkylene)glycol, and Q is a divalent organic radical.

Preferred polyalkylene glycol terephtalates are chosen from the group of polyethylene glycol terephtalate, polypropylene glycol terephtalate, and polybutylene glycol terephtalate and copolymers thereof, such as poloxamers. A highly preferred polyalkylene glycol terephtalate is polyethylene glycol terephtalate.

Furthermore, in order to facilitate acceptance of the artificial pancreas as a therapy in the clinic, it is beneficial when the polymer used for the first layer is FDA approved. An example of such a polymer is a copolymer comprising a polyethylene glycol terephtalate (PEGT) (soft) block and polybutylene-terephatalate (PBT) (hard) block, according to formula (I):

In case the material from which the first layer is made is not porous itself, electrospinning may be used to prepare material with a desirable porosity. For example, a polymeric first layer may be obtained by electrospinning a viscoelastic polymer solution. A polymer particularly suitable for forming a first layer of the porous scaffold of the invention is for example PolyActive™.

The technique of electrospinning is known in the art per se. The skilled person will know how to suitably use this technique. It is shortly discussed below.

In electrospinning, nanofibers are produced by uniaxial stretching of a viscoelastic solution in which the material is dissolved. Typical materials used are natural or synthetic polymers. Electrospinning uses electrostatic forces to 'stretch' the polymer solution, which may be pumped through a needle/spinneret, into very thin nanofibers, thereby increasing the solidification speed of the material. The fibers are more or less 'spun down' and collected. A critical voltage is applied to the solution resulting in the induction of the polymer's charge and charge repulsion within the solution. The electrical field deforms the shape of the liquid in such a way that the liquid forms a cone like shape which originates at the tip of the spinneret, which is called the Taylor cone. Eventually, the repulsion charge within the solution will exceed the surface tension forces

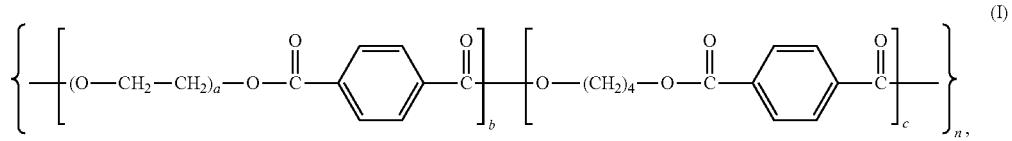

wherein a represents the polyethylene glycol (PEG) weight (MW g/mol) of the PEG segment that is enclosed in the PEOT block, and wherein b and c represent the weight percentage (wt. %) of PEGT and PBT based on the total copolymer weight. The initial length of the polyethylene glycol (PEG) segment can be varied, as can be the molar ratio of the PEGT to PBT segments. Such a copolymer may be obtained under the trade name Polyactive™.

Advantage of using the copolymer according to formula (I) is that the physicochemical properties of the polymer may easily be tailored by varying the weight ratios of the two blocks and/or the molecular weight of the soft block. Thus, these adjustments may allow for adjustment of degradability, elasticity and hydrophobicity. Another advantage of the PEGT-PBT copolymers is that they can easily be used for rapid prototyping, by electrospinning, hot-embossing, solvent-casting, compression molding and 3D fiber deposition. Moreover, this copolymer is FDA approved and has been tested in numerous clinical trials and is currently used in patients for orthopedic, skin and drug-delivery applications.

Preferably, the polymer used for the first layer is flexible. Preferably, the first layer is biocompatible, preferably non-cytotoxic and preferably biodegradable.

The first layer may be dense. However, the first layer is preferably porous, as described below.

The first layer is preferably based on a porous material. For example, the first layer may essentially consist of the porous material. The porous material may have pores having an average diameter of 10-200 µm. The presence of pores in the first layer allows blood vessels to penetrate the first layer when implanted in the human body. The blood vessels may thus support the islets of Langerhans with nutrients.

and a so called polymer jet is created. The jet is stable near the tip of the spinneret but gets unstable when the distance from the tip is increasing due to imbalances in the charge distribution. This causes the jet to bend randomly. Furthermore, the jet will stretch even more upon evaporation of the solvent. The fibers are collected by a grounded collector, which consists of a conducting material resulting in the attraction of the fibers. Subsequently, a non-woven mesh of nanofibers is collected. Preferably, the beta cell aggregates are not encapsulated in the first layer.

The second layer is preferably biocompatible, non-cytotoxic and biodegradable. The second layer may be used for layering the first polymer layer by either stacking the polymer layers or rolling them using hydrogel as a bonding layer. Thus, the beta cell aggregates may be protected and retain their three-dimensional structure while still allowing for diffusion of nutrients and insulin and cell ingrowth. One of the advantages of the second layer is that the second layer may hold the beta cell aggregates in place, for example by preventing the beta cell aggregates from exiting the microwells, both during and after implementing the scaffold in the human body. In one embodiment, the second layer seals the microwells.

An example of a widely used hydrogel that is also suitable as a second layer in the present invention is the polymer poly(2-hydroxyethyl methacrylate) (poly-Hema). Other examples of suitable hydrogels are alginates; agarose; collagen derived hydrogels; platelet derived hydrogels; pluronic acid derived hydrogels; hydrogels of natural polymers, such as dextran, hyaluronic acid, chitosan, chondroitin sulphate, heparin, heparin sulphate or combinations thereof; and combinations thereof.

Preferably, the polymer used for the second layer is flexible. Preferably, the polymer used for the second layer is biocompatible, preferably non-cytotoxic and also preferably biodegradable.

In one embodiment, the second layer may be made of platelet derived gel or fibrin gel. Such a gel may be obtained by platelets mediating the clotting of plasma-borne fibrinogen. The platelets may be isolated from the blood of the patient for which the scaffold is intended. Subsequently, a gel can be made prepared from these isolated platelets. The platelet derived gel may further comprise natural growth factors. The platelets may also further be purified to obtain a fibrin gel. The use of platelet derived gel and fibrin gel is advantageous, because it is material that can be obtained from the body for which the scaffold is intended. Furthermore, a second layer made of platelet derived gel or fibrin gel may promote the ingrowth of blood vessels in the scaffold.

The second layer may further be used as a drug delivery vehicle. For example, the second layer may comprise growth factors. Such growth factors may stimulate cell survival and blood vessel ingrowth in the scaffold. Growth factors may further be used for the proliferation and differentiation of different cell types involved.

The scaffold of the invention may further comprise growth factors, preferably incorporated in the second layer, which attract and/or stimulate blood vessel formation and/or blood vessel forming cells (endothelial cells). Thus, the scaffold may rapidly connect to the patient's bloodstream after implantation. Example of such growth factors are angiogenis factors that stimulate vessel formation, e.g. angiogenin, angiopoietin-1, developmental endothelial locus-1 (del-1), fibroblast growth factors (FGF), such as fibroblast growth factors acidic (aFGF) and basic fibroblast growth factors (bFGF), follistatin, leptin, placental growth factor, tumor necrosis factor-alpha (TNF-alpha) and vascular endothelial growth factor (VEGF). Furthermore, growth factors may be present in the scaffold, in particular in the second layer, to increase survival chances of the beta cells.

The scaffold according to the invention has very good properties for releasing insulin and/or detecting glucose levels in the body. Beside insulin producing cells (viz. the beta cells), a beta cell aggregate may comprise other hormone producing cells, for example a glucagon producing cell. For proper functioning of the scaffold however, release of such other hormones does not appear vital, although it may improve the overall functioning of the scaffold. The agglomerates in the scaffold may retain their morphology and respond to a rise in glucose by secretion of insulin. It was further found that the scaffold of the invention was very suitable for preventing migration, e.g. beta cell migration. When used as implants, the agglomerates have a high chance of survival and may be incorporated in the body functioning as an artificial pancreas. The scaffold according to the invention may be suitably used as an implant in the human body.

The scaffold may be a controlled drug delivery device. The beta cells sense the glucose levels in the patient and produce insulin accordingly. The beta cells may further secrete amylin and glucagon. The scaffold is intended to mimic the function of the Langerhans Islets as close as possible. By using a scaffold in which beta cell aggregates have formed, which resemble the Langerhans islets in the body, an insulin producing artificial organ, which uses the sensing capabilities of the beta cells themselves to respond to glucose concentrations. In addition, it is possible to use the capabilities of the used polymeric scaffold and/or the hydrogel to act as a drug delivery device to stimulate blood vessel formation.

In a second aspect, the invention is directed to the scaffold according to the first aspect for use in the treatment of diabetes.

The scaffold of the first aspect is in particular suitable for the treatment of diabetes type I. However, it may be understood that patients suffering from other types of diabetes may also benefit from the treatment according to the present invention.

The treatment may comprise surgically implanting a scaffold according to the first aspect in a human or animal body, for example near the liver. Preferably, the scaffold comprises small beta cell aggregates, as described hereinabove. Because of the increased efficiency of small aggregates, less islets of Langerhans are needed for treating diabetes compared to prior art treatments, which is very desirable due to the current lack of donor pancreata.

In a third aspect, the invention is directed to a method for preparing the scaffold of the first aspect, comprising the steps of:
  isolating islets of langerhans from a pancreas; and
  optional size fractionation of the obtained islet cells, e.g. by using filters; and
  providing a polymer layer comprising microwells; and
  seeding the microwells with beta cell agglomerates originating from the isolated islet of Langerhans, e.g. by formation of beta cell aggregates in the microwells of the scaffold; and
  covering the microwells with a hydrogel layer.

The polymer layer comprising microwells refers to the first layer of the scaffold of the invention. The hydrogel layer refers to the second layer of the scaffold of the invention.

The properties of the first layer (or polymer layer), second layer and microwells described above for the scaffold according to the invention also apply for the method of the invention.

The beta cell agglomerates originating from the isolated islet of Langerhans are preferably the islets of Langerhans isolated in the first step of the method. Such islets and their desired properties have already been described above for the scaffold according to the invention and also apply to the method of the invention.

Preferably, the islets of Langerhans isolated from a pancreas are seeded in the microwells directly. This means that the islets of Langerhans are seeded without subjecting them to any treatment between isolation and seeding other than providing suitable conditions for keeping the islet of Langerhans alive and functional, e.g. in a culture medium. Thus, the favorable morphology of the islets of Langerhans as they were present in the pancreas from which they were isolated is maintained. Isolated islets of Langerhans consist mainly of differentiated cells. It was found that no substantial cell growth takes place in these differentiated cells, at least not before the scaffold is implanted in the body. This is advantageous, because in this way, the islet of Langerhans can maintain their favorable morphology when initially placed in the microwells.

The average size of the islets of Langerhans that are seeded in the microwells is preferably small enough to suitably fit in the microwells, e.g. 250 µm or less. Since both small islets (less than 50 µm), regular sized islets (50 -150) and big islets (150-200 µm and 200-250 µm) may be functional, these can all be used for seeding. However, islets that are too large, in particular those having a diameter larger than 250 µm, have a lower survivability and may not fit in the microwells and are therefore less or not suitable to use.

The average number of cells that are seeded in the microwells is typically at least 50 cells (for example at least 200 or at least 400 cells) and at most 4000 cells (for example 2500 cells or less, 1500 cells or less, or 500 cells or less).

Cell growth of the beta cell aggregates after seeding them in the microwells should be avoided. Cell growth may lead to the beta cell aggregates becoming too large for the microwells they are seeded in. Consequently, the beta cell aggregates will break out of the microwells, such that they are no longer separated from each other by polymer material. As a result, the beta cell aggregates may even grow further and connect with other beta cell aggregates from different microwells. Thus, cell growth of the beta cell aggregates may result in two or more beta cell aggregates from different microwells to merge into one large beta cell aggregate. Such merging of beta cell aggregates from different microwells is undesirable, because the aggregates thus loose their favorable morphology, in particular when isolated islets of Langerhans are used. It was further found that merging islets of Langerhans may dedifferentiate, which may lead to cell growth and undesirable loss of morphology, undersirable loss of function and/or apoptosis.

A number of measures can be made to prevent the cell aggregates, in particular islet of Langerhans, from merging together after seeding them in the microwells. Most of these are described above and include applying a second layer on top of the first layer, thus preventing the beta cell aggregates from exiting the microwells;

using isolated islets of Langerhans, which are differentiated cells and therefore will substantially not proliferate;

provide microwells that have a large enough size to contain the beta cell aggregate to be seeded;

It was further found that islet cells having a small diameter (e.g. <180 µm) were more active in producing insulin and have a better chance of surviving after implantation than islets cells having a large diameter (e.g. >180 µm). Therefore, the beta cell aggregates preferably have a diameter of less than 350 µm, more preferably a diameter of 250 µm or less, even more preferably a diameter of 150 µm or less, most preferably a diameter of 100 µm or less. Typically, the aggregate has a minimum diameter of at least 20 µm, more preferably at least 50 µm.

To prepare beta cell aggregates having a suitable small size, isolated islets of Langerhans may be size fractionated. It was found that isolated islets of Langerhans could be very suitably size fractionated by using filters, in particular cell strainers. The method of the invention may therefore further comprise the steps of:

a first filtration step, wherein isolated islets of Langerhans filtrated through a first filter having a first pore size; and an optional second filtration step, wherein the filtrate of the first filtration step is filtrated through a second filter having a second pore size smaller than the first pore size.

Optionally, a third and further filtration step may be conducted each time using the filtrate of the previous filtration step, using a filter with a smaller pore size in every subsequent filtration step.

The first filter may have a pore size of 20-200 µm, more preferably a pore size of 50-160 µm, even more preferably a pore size of 100-150 µm.

For example, the isolated islets of Langerhans may first be filtered through a filter with a 150 µm pore size, thus obtaining a first filtrate. Subsequently, the first filtrate may be filtered through a filter with a 100 µm, thus obtaining a second filtrate. Subsequently, the second filtrate is filtered through a third filter with a 50 µm pore size.

Filters suitable for use in the present invention are for example cell strainers made of a monofil nylon material, which can be obtained from BD Falcon® (100 µm pore size) and CellTrics® (150 µm and 50 µm pore size).

It was found that during size fractionation, bigger islets may fall apart into two or more smaller islets. Without wishing to be bound by theory, it is expected that the number of islets with a diameters above 100 µm is decreased and islets with a diameter between 50 and 100 µm is increased by size fractionation of islets of Langerhans.

Beta cells having a suitable small particle size may be used for seeding the microwells.

The bigger islets may be suspended to obtain single cell suspension. Subsequently, the cells in the suspension may be reassembled into small aggregates, e.g. by aggregation of the suspension in microwells. These small aggregates may be used again in preparing a scaffold of the first aspect.

Since smaller aggregates are more efficient and have a higher chance of survival after implantation as described hereinabove, the invention allows for a more efficient use of isolated islets of Langerhans and thus a more efficient use of donor pancreata. This is very desirable due to the current lack of donor pancreata.

The method of the present invention may further comprise the step of preparing a polymer scaffold comprising microwells.

Figure 7:
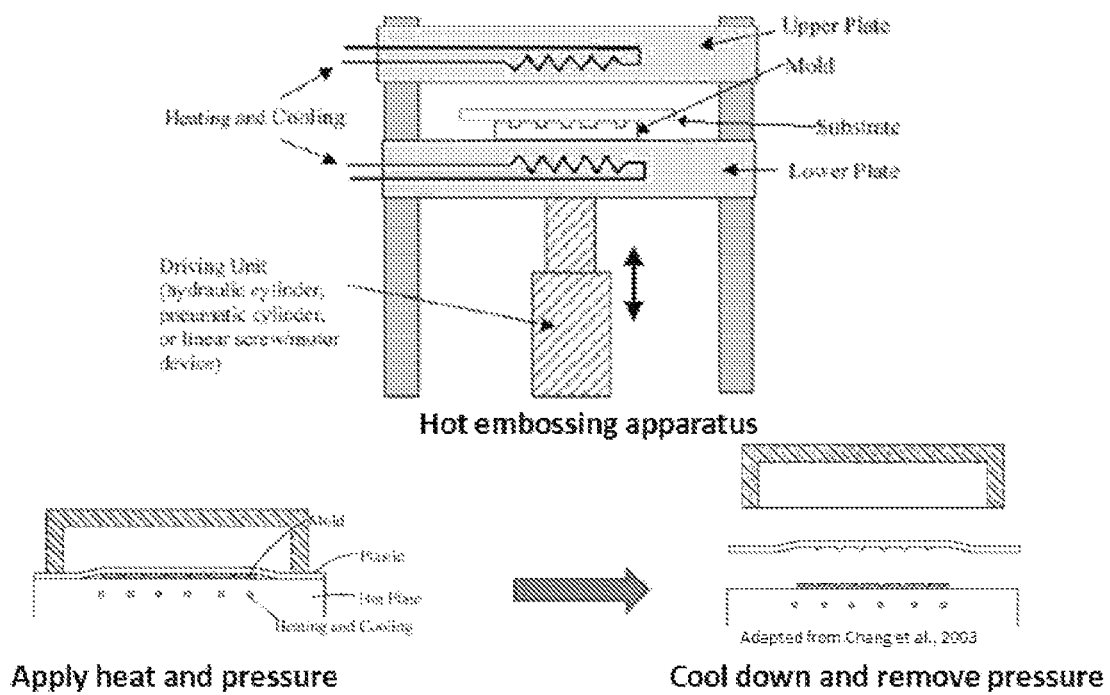
FIG. 7 is a schematic representation of the hot embossing technique which may be used for preparing microwells in the scaffold of the invention.

To prepare a polymer scaffold comprising microwells, a technique called hot embossing may be used. An example of the hot embossing technique is depicted in FIG. 7. Firstly, a polymer substrate is heated, preferably to a temperature above the glass transition temperature (Tg) of the polymer. Secondly, a mold, e.g. a stamp or master, is pressed against the substrate for an amount of time sufficient to allow the pattern to be fully transferred onto the substrate (embossing), e.g. about five minutes. Thirdly, the molded polymer substrate is then cooled down below Tg and subsequently separated from the mold (de-embossing). The thus obtained polymer substrate may be sterilized, e.g. by placing it in ethanol for several minutes, e.g. about 20 minutes.

Pressing of the mold to the substrate may be conducted in a press machine comprising hot press plates. The substrate may in such a case be pressed directly by the hot plates of the press machine. Thus, heating and pressing may take place within one pressing machine.

The polymer substrate may be made of polypropylene (PP), polylactide (PLA), polycarbonate (PC) and cyclic olefin polymer (COP), polypropylene (PP), poly(lactic-co-glycolic acid) (PLGA), polyurethane (PU), PU derived biomaterials, poly(trimethylene carbonate), caprolactone and copolymer of a polyalkylene glycol terephtalate and an aromatic polyester.

The mold used may be a steel template, preferably a laser etched steel template. Preferably, the mold has an inverted microwell structure, i.e. the mold comprises protrusions that, when pressed to a substrate, are capable of forming microwells in the substrate. The mold may have protrusions having the same diameter as the desired diameter of the microwells, i.e. a diameter of 20-800 µm, more preferably 40-500 µm, most preferably 100-350 µm. A microwell may have any shape, but is preferably essentially circular shaped.

The scaffold may be chemically treated prior to adding the beta cell aggregates to improve the cell adherence of the beta cells to the scaffold. An example of a chemical treatment is a plasma treatment such as an oxygen plasma treatment or an argon plasma treatment.

The method of the invention may further comprise the formation of aggregates in microwells of a scaffold comprising a surface comprising microwells. First, a fixed number cells, which cells comprise beta cells, are seeded in a microwell of the scaffold. To obtain a desirable diameter, the number of cells placed in one microwell may be 20-500, preferably 40-400, more preferably 50-200 cells. Preferably, at least 20% of these cells are beta cells, more preferably at least 50%, even more preferably at least 70%, most preferably at least 90%. The scaffold preferably comprises at least 1 million microwells and at most 5 million microwells. From these data, one could calculate the total number of beta cells present in a scaffold according to the invention. Subsequently, the cells are centrifuged into the wells after which they start forming aggregates.

Alternatively, aggregates may be formed using the hanging drop method. In this method, cells are suspended in a solution and then pipetted into wells. By inverting the plate, i.e. turning it upside down, carefully, drops will be formed. Due to gravity, the cells may accumulate at the meniscus of the drop and thus start forming an aggregate.

The present invention will be further illustrated by the following examples.

EXAMPLE 1

Islet Isolation

Human islets of Langerhans were isolated from the pancreas from braindead humans. The tissue was kept at standard cell culture conditions, viz. in an atmosphere comprising 5 vol. % of $CO_2$ and 95 vol. % at a temperature of 37° C., for no longer than 5 days after the isolation procedure. The medium used was CMRL-1066 (5.5 mM glucose), 10% fetal bovine serum (FBS), 0.1 mg/ml streptomycin and 100 U/ml penicillin. Three batches of tissue with 10 to 25% purity were used for size fractionation, wherein the islets were fractionized using three cell strainers of respectively 150 μm, 100 μm and 50 μM.

EXAMPLE 2

Size Fractionation

An islet of Langerhans dispersion was filtrated through a filter comprising three monofil nylon cell strainers stacked on top of each other, the three cell strainers having a pore size of successively 150 μm, 100 μm and 50 um. The cell strainers were wetted with medium before pipetting the pancreatic tissue into them drop by drop. After filtration each filter was turned upside down and was flushed vigorously with medium into 50 ml tubes. Then, the tubes were spinned at 1500 rpm for 2 minutes. The supernatant was removed and the islets were resuspended in a smaller volume, e.g. about 4 ml.

EXAMPLE 3

Mold Fabrication

Stainless steel molds have been machined using a femtosecond pulsed laser system: Coherent RegA 9000+Coherent Vitesse duo, which is based on Ti:Sapph as gain material. The laser delivers 200 fs pulses at a repetition frequency of 250 kHz. The pulse energy of the system is 4 μJ, leading to a power of 1 W. A galvo scanner was used for manipulation of the laser bundle over the work piece. A 100 mm lens was used to focus the beam to a spot of 25 μm. The depth of the mold was demanded to be 200-300 μm. In order to machine to such depths a relatively wide trench has to be machined, as tapering leads to a natural stop of a trenches depth. Here, for every trench 8 lines are machined at a spacing of 12 μm. The spacing of the trenches is 250 μm. The whole pattern was repeated 300 times.

EXAMPLE 4

Scaffold Preparation

Using the hot embossing technique and the mold from example 3, a polymer scaffold comprising microwells was made from a PEOT/PBT substrate.

Figure 2:
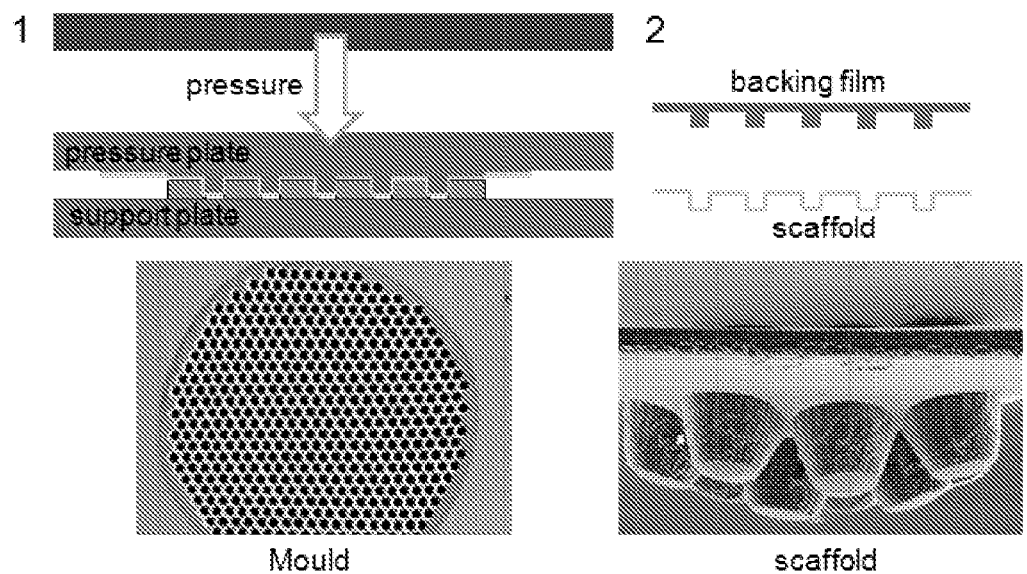
FIG. 2 shows a schematic representation of a molding technique which may be suitably used in the present invention.

FIG. 2 shows a schematic representation of the molding technique used. In between two support plates the polymer sheet (light grey) is placed on top of the mould (dark-grey) on which a socalled backing film is subsequently placed consisting of a soft elastomeric polymer. The backing film and polymer sheet is then pushed into the mould by pressurizing the support plates using a temperature controlled press (Step 1). After pressing the backing film and polymer are removed from the mould and the backing film is peeled off, after which a micro-well container scaffold remains (step 2). In the bottom panel stainless steel mould, showing an array of laser drilled holes and a side view of a dense microwell scaffold sample are depicted by scanning electron microscopy.

EXAMPLE 5

Seeding

Scaffolds were seeded with human or rat derived islets of Langerhans with a diameter of <130 μm and >180 μm respectively. After seeding functional tests were performed to check for insulin production using ELISA. After seeding islets retained their proper morphology and respond to a rise in glucose in the culture medium by secretion of insulin.

EXAMPLE 6

Cytoxicity Test

Cytotoxicity tests were done by adding extracts of the PEOT/PBT copolymer to MC3T3-E1 cells. PLA was used as a control. The tests showed that PEOT/PBT samples were well within the non to slight cytotoxicity range and were comparable in cytotoxicity to PLA samples.

EXAMPLE 7

Contact Angle Measurement

Contact angle measurement that the scaffold treated after oxygen plasma treatment had a slightly lower wet angle than the non-plasma treated samples, 82-80 degrees for the non heated and heated samples for Polyactive polymer samples (PEOT/PBT). The same observation was made for polylactic acid (PLA). In addition heating without treatment also lowered the wet angle.

EXAMPLE 8

Preparing a Porous Scaffold Sheet

PolyActiveTM PA (type 4000PEGT30PBT70) was dissolved in a mixture of chloroform (CH3Cl) and hexafluoroisopropanol (HFIP) (78%/22% v/v). Both solvents were ordered from Sigma-Aldrich. A polymer concentration of 0.15 g/ml was used and the solution was left overnight to let the polymer dissolve properly. During the electrospinning process, a voltage of 18 kV was applied to obtain a stable jet. The flow rate was set at 2 ml/h and the height between the nozzle and the collecting plate was set at 10 cm. A 5 ml syringe was filled with polymer solution (5 ml in total) and connected to a needle (18 G). The needle was attached to a Teflon tube (1.07×1.67 mm) which was subsequently connected to a nozzle. Environmental conditions were monitored during the process: the temperature and humidity were 21.4° C. and 39% respectively. PA (type 300PEGT55PBT45) was dissolved in CH3Cl and HFIP (78%/22% v/v) at a concentration of 0.28 g/ml. A voltage of 12 kV was applied, the flow rate was set at 20 ml/h and the height between the nozzle and the collecting plate was 15 cm. The temperature and humidity were 21.4° C. and 33%. The thermoforming of the containers was done by cutting a piece of the electrospun sheet and putting it on top of the mould so that the area with the microwells was completely covered. Polyethylene (PE) films (12 pieces) with a thickness of 0.05 mm each were put on top of the electrospun sample to press the PA sheet into the mould. Everything was put between two plates of stainless steel before placing it in the press. Subsequently, the metal support plates of the press were closed, but to such an extent that there was still no pressure applied to the sample. The press was heated to a temperature of 80° C. which was reached after about 15 minutes. After that, the plates of the press were pushed together so that a pressure of about 10 kN was applied. Immediately after applying the pressure, the plates were cooled down with cold water. After about 20 minutes until the sample was cooled down, the pressure was released and the sample was detached from the mould.

EXAMPLE 9

Morphology of Dense and Porous Layer

Figure 3:
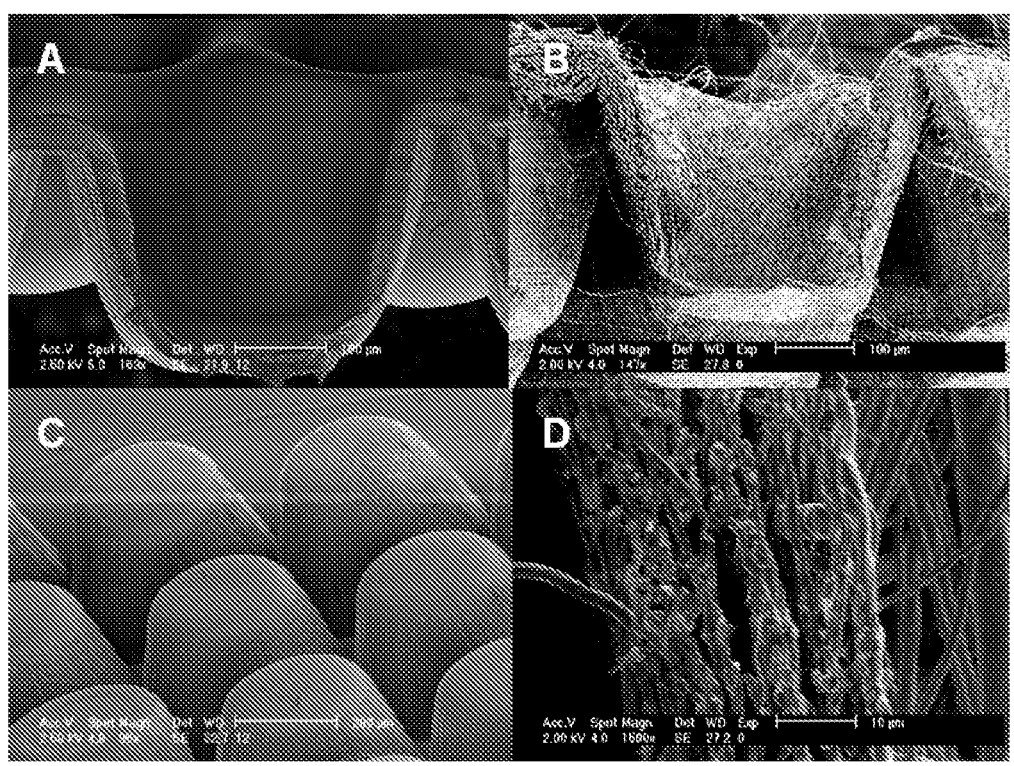
FIG. 3 shows scanning electron micrographs of the morphology of two scaffolds comprising microwells according to the invention, one with a dense first layer (FIGS. 3A and 3C) and one with a porous first layer (FIGS. 3B and 3D).

A dense and a porous first layer according to the invention, which first layer comprises microwells, were studied using Scanning Electron Microscope. The results are shown in FIG. 3. FIG. 3 shows i.a. the uniform distribution of the wells (FIG. 3C) and the porosity of the porous microwell scaffold sidewalls (FIG. 3D).

EXAMPLE 10

Functional Insulin Secretion Assay

Free non seeded human islets of three human donors were compared with seeded islets in scaffolds comprising microwells. Both scaffolds having a small diameter (~100 µm) and scaffolds having a large diameter (~150-200 µm) were tested. The results of the tests are shown in FIG. 4.

Figure 4:
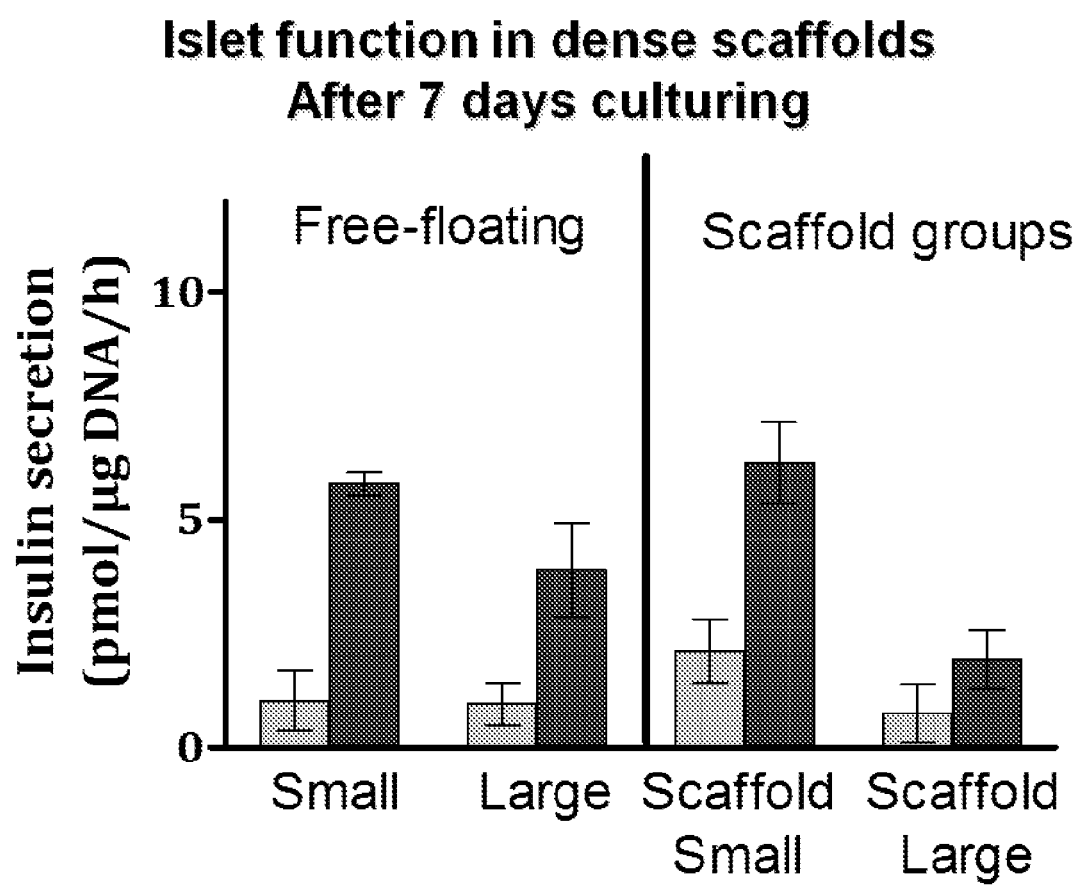
FIG. 4 is a graph showing a functional insulin secretion assay.

FIG. 4 shows the basal insulin secretion in light gray, both of small diameter islets and of large diameter islets, after challenging with a 1.7 mM glucose concentration and in dark grey the insulin secretion after challenging with a 16.7 mM glucose concentration after 7 days of culture. The increase in insulin secretion shows the active response of the islets after 7 days of culture with and without microwell scaffold. The response between the free floating and scaffold group do not differ significantly.

EXAMPLE 11

Effect of Polymer Surface on Islet Adherence

Figure 5:
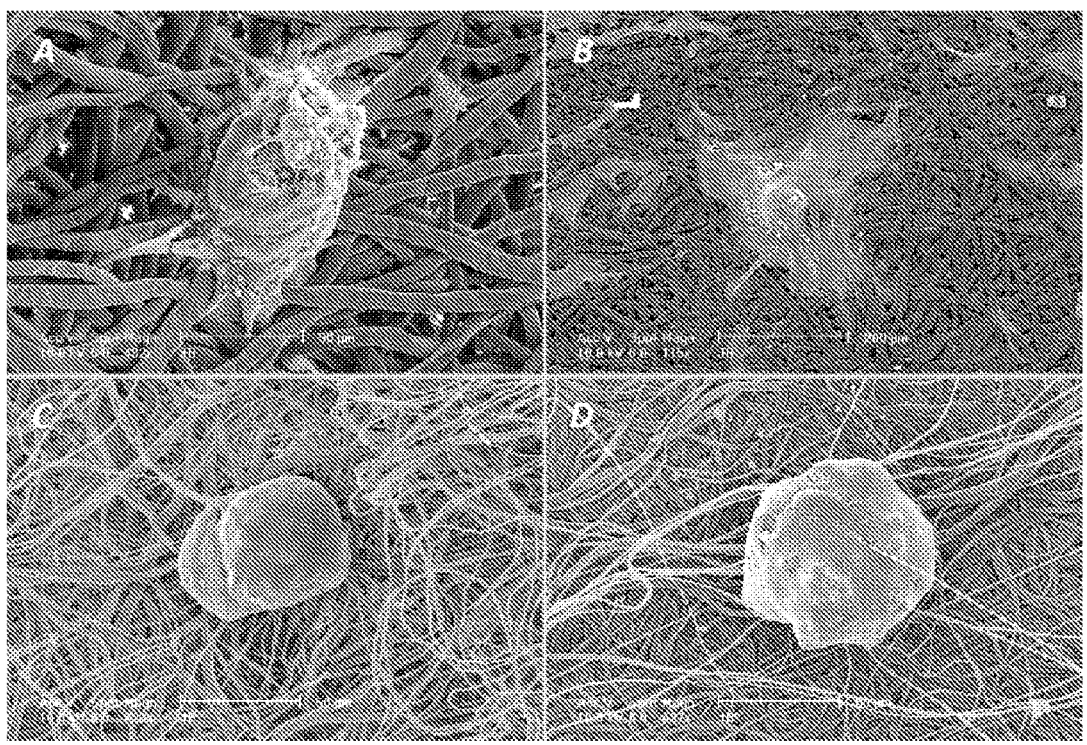
FIG. 5 shows four SEM images of islets in contact with scaffolds made of different polymer compositions.

Two week old human Langerhans islets were cultured on two diferent electrospun PolyActive scaffolds, viz. 300-PEGT-55-PBT-45 (PA1) and electrospun 4000-PEGT-30-PBT-70 (PA2) scaffolds. The scaffolds comprising the islets were analyzed using SEM. The results are shown in FIG. 5.

FIG. 5A shows the islets cultured on PA1 scaffolds at day 3.

FIG. 5B shows the islets cultured on PA1 scaffolds at day 12.

FIG. 5C shows the islets cultured on PA2 scaffolds at day 3.

FIG. 5D shows the islets cultured on PA2 scaffolds at day 12.

The PA2 polymer has almost no effect on islet morphology while the PA1 polymer shows adherence and outgrowth of cells from the islets ultimately leading to flattening and loss of spherical morphology.

It was concluded that because of the more hydrophilic nature and chemical composition of the PA1 scaffold (PA1 has a lower concentration of the hydrophobic PBT block), the scaffold comprised of PA2 material was more suitable to serve as a microwell scaffold, since almost no cell spreading and adherence was observed.

EXAMPLE 12

Lighmicrographs of Human Islets of Langerhans

Figure 6:
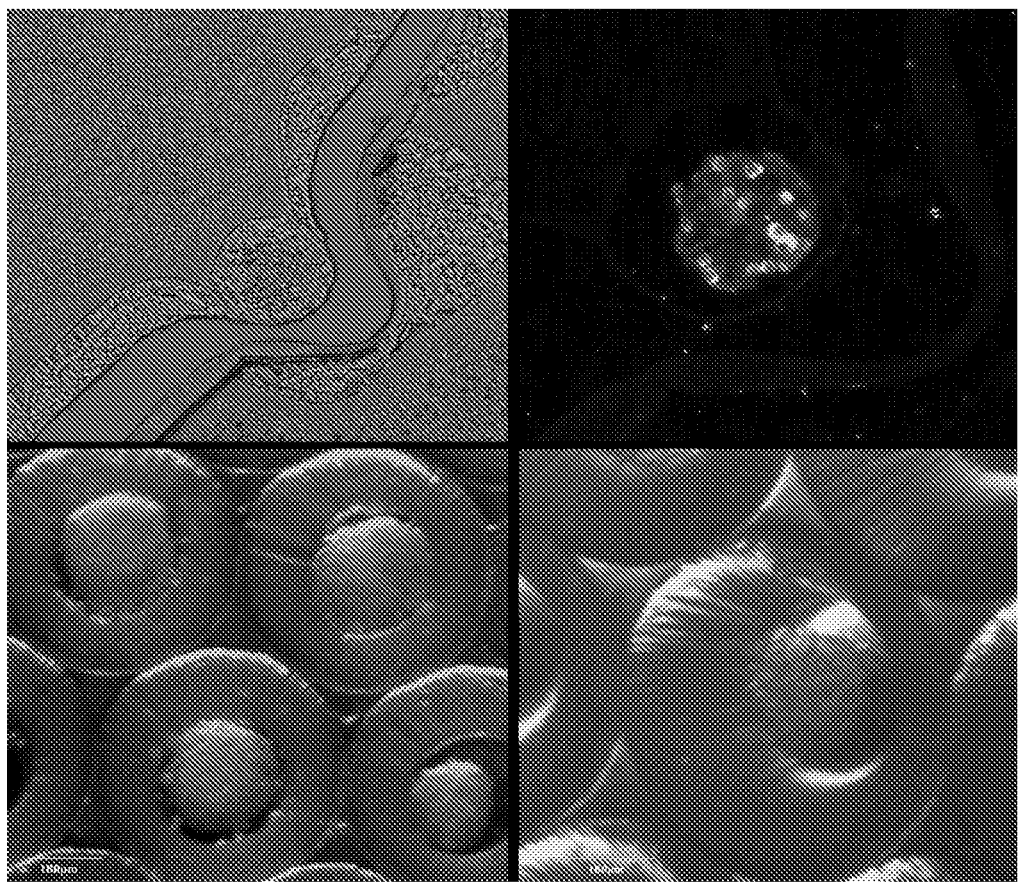
FIG. 6 shows light micrographs of islet cells in microwells in a scaffold of the invention.

Human islets of Langerhans were cultured for 7 days in microwell scaffolds. They were then analyzed using a light microscope. FIG. 6 shows the results of the analysis.

Top left panel of FIG. 6 shows the cross-section of an islet inside a microwell, showing the still rounded morphology.

The top right panel of FIG. 6 shows the same sample stained for insulin, glucagon and DNA using fluorescent labeling.

The bottom panels of FIG. 6 show a top view of several islets inside microwell containers showing their rounded morphology.

The invention claimed is:

1. An implantable scaffold comprising a first layer which is a hydrophobic polymer layer that comprises a surface comprising molded, discrete microwells, wherein each microwell has a diameter of 20-800 µm and wherein said microwells contain beta cell aggregates so that the beta cell aggregates are distributed over the scaffold in a predetermined pattern of said microwells.

2. The implantable scaffold according to claim 1 wherein the beta cell aggregates are islets of Langerhans isolated from a donor pancreas.

3. The implantable scaffold according to claim 1, wherein the first layer is a porous layer.

4. The implantable scaffold according to claim 1, wherein the scaffold sheet further comprises a second layer.

5. The implantable scaffold according to claim 4, wherein the second layer is a hydrogel layer.

6. The implantable scaffold according to claim 1, wherein each beta cell aggregate has a diameter of less than 180 μm, as measured with a scanning electron microscope.

7. The implantable scaffold according to claim 1, wherein each beta cell aggregate comprises 20-500 cells.

8. The implantable scaffold according to claim 1, wherein the first hydrophobic polymer layer is a layer having substantially no adherence with the beta cell aggregates.

9. The implantable scaffold according to claim 4, wherein the hydrogel layer seals the microwells, thus encapsulating the beta cell agglomerates in the scaffold.

10. The implantable scaffold according to claim 4, wherein the hydrogel layer is made of a material selected from the group consisting of poly(2-hydroxyethyl methacrylate); alginates; agarose; collagen derived hydrogels; platelet derived hydrogels; pluronic acid derived hydrogels; hydrogels of dextran, hyaluronic acid, chitosan, or heparin; and a combination thereof.

11. The implantable scaffold according to claim 1, wherein the first hydrophobic polymer layer is made of a material selected from the group consisting of polylactic acid (PLA), polypropylene (PP), polycarbonate (PC), cyclic olefin polymer (COP), poly(trimethylene carbonate), caprolactone, poly(lactic-co-glycolic acid) (PLGA), polyurethane (PU), PU derived biomaterials and a copolymer of a polyalkylene glycol terephthalate and an aromatic polyester.

12. The implantable scaffold according to claim 1, further comprising growth factors and/or factors that stimulate survival of beta cells.

13. A method to treat diabetes which comprises implanting the scaffold according to claim 1 into a subject in need of such treatment.

14. Method for preparing the implantable scaffold according to claim 2, comprising the steps of:
providing isolated islets of Langerhans from a pancreas; and
providing a hydrophobic polymer layer comprising molded, discrete microwells; and
seeding the microwells with beta cell agglomerates originating from the isolated islets of Langerhans; and
covering the microwells with a hydrogel layer.

15. Method according to claim 14, wherein the islets of Langerhans are directly seeded in the microwells.

16. Method according to claim 14, wherein the microwells have an average diameter of 100-350 μm.

17. Method according to claim 14, further comprising the step of size fractionation of the obtained islets of Langerhans cells prior to seeding.

18. The implantable scaffold according to claim 4 wherein the hydrogel layer incorporates growth factors and/or factors that stimulate survival of beta cells.

19. An implantable scaffold comprising a first layer which is a hydrophobic polymer layer that comprises a surface comprising molded, discrete microwells, wherein each microwell has a diameter of 40-500 μm and wherein said microwells contain beta cell aggregates so that the beta cell aggregates are distributed over the scaffold in a predetermined pattern of said microwells.

20. The implantable scaffold according to claim 5, wherein the hydrogel layer is a fibrin or platelet derived gel layer.

* * * * *